(12) United States Patent
Lee et al.

(10) Patent No.: US 6,581,234 B2
(45) Date of Patent: Jun. 24, 2003

(54) DENTAL BRUSH UNIT COMPRISING GEAR CONNECTIONS

(76) Inventors: Jin Po Lee, 7348 Melodia Ter., Carlsbad, CA (US) 92009; Cheng-Chieh Chiang, 2F., 24, Lane 80, Section 1, Tung-Hwa South Rd., Taipei (TW)

(*) Notice: Subject to any disclaimer, the term of this patent is extended or adjusted under 35 U.S.C. 154(b) by 0 days.

(21) Appl. No.: 09/824,854

(22) Filed: Apr. 2, 2001

(65) Prior Publication Data
US 2002/0138927 A1 Oct. 3, 2002

(51) Int. Cl.[7] .............................. A46B 7/08; A61C 17/16
(52) U.S. Cl. .............................................. 15/28; 15/22.1
(58) Field of Search ............................. 15/22.1, 28, 29

(56) References Cited

U.S. PATENT DOCUMENTS

| | | | |
|---|---|---|---|
| 1,391,221 A | * | 9/1921 | Tuttle |
| 1,997,352 A | * | 4/1935 | Van Fleet |
| D266,117 S | | 9/1982 | Oberheim |
| 5,289,604 A | | 3/1994 | Kressner ..................... 15/22.1 |
| 5,309,591 A | | 5/1994 | Hagele et al. ................ 15/22.1 |
| 5,359,747 A | * | 11/1994 | Amakasu |
| D353,490 S | | 12/1994 | Hartwein |
| 5,467,495 A | | 11/1995 | Boland et al. .................. 15/28 |
| 5,499,420 A | | 3/1996 | Boland ....................... 15/22.1 |
| 5,504,958 A | | 4/1996 | Herzog ........................ 15/22.1 |
| 5,577,285 A | | 11/1996 | Drossler ...................... 15/22.1 |
| 5,652,990 A | | 8/1997 | Driesen et al. ................. 15/28 |
| D388,958 S | | 1/1998 | Hartwein |
| 5,732,433 A | | 3/1998 | Gocking et al. ................ 15/28 |
| 5,784,743 A | * | 7/1998 | Shek |
| 5,842,244 A | | 12/1998 | Hilfinger et al. ............. 15/22.1 |
| 5,850,655 A | | 12/1998 | Gocking et al. ................ 15/28 |
| 5,862,558 A | | 1/1999 | Hilfinger et al. ................ 15/28 |
| 5,867,856 A | | 2/1999 | Herzog ........................ 15/22.4 |
| 5,943,723 A | | 8/1999 | Hilfinger et al. ............. 15/22.1 |
| 5,974,613 A | | 11/1999 | Herzog ........................ 15/22.1 |
| 5,974,615 A | | 11/1999 | Schwarz-Hartmann et al. ........................ 15/22.4 |
| 6,009,589 A | | 1/2000 | Driesen et al. ............. 15/167.1 |
| 6,021,538 A | | 2/2000 | Kressner et al. ................ 15/28 |
| 6,094,769 A | | 8/2000 | Driesen et al. ............ 15/207.2 |
| 6,363,565 B1 | * | 4/2002 | Paffrath |
| 6,367,108 B1 | * | 4/2002 | Fritsch |
| 6,381,795 B1 | * | 5/2002 | Hofmann et al. |

FOREIGN PATENT DOCUMENTS

EP            0 500 537            11/1994

* cited by examiner

*Primary Examiner*—Terrence R. Till
(74) *Attorney, Agent, or Firm*—Morrison & Foerster LLP

(57) ABSTRACT

The present invention relates to replaceable dental brush units useful in an electric toothbrush. In particular, the invention provides for a replaceable dental brush unit useful in an electric toothbrush that uses gear links for connecting and driving motions of bristle head by motors.

20 Claims, 4 Drawing Sheets

DENTAL BRUSH UNIT COMPRISING GEAR CONNECTIONS

CROSS-REFERENCE TO RELATED APPLICATIONS

Not Applicable

STATEMENT REGARDING FEDERALLY SPONSORED RESEARCH OR DEVELOPMENT

Not Applicable

INCORPORATED-BY-REFERENCE OF MATERIAL SUBMITTED ON A COMPACT DISC or REFERENCE TO A MICROFICHE APPENDIX

Not Applicable

BACKGROUND OF THE INVENTION

The present invention relates to replaceable dental brush units useful in an electric toothbrush. In particular, the invention provides for a replaceable dental brush unit useful in an electric toothbrush that uses gear links for connecting and driving motions of bristle head by motors.

Electric toothbrushes are known and widely used (See e.g., U.S. Pat. Nos. 5,289,604 and 5,974,615). U.S. Pat. No. 5,289,604 discloses an electric toothbrush having a brush section which is demountable from a handle section that has a protruding brush drive shaft. Radial and axial securing of the brush section to the handle section is accomplished by structure separated by function, including radial securing structure at the base of the brush section that engages cooperating structure at the end of the handle section from which the drive shaft protrudes, and axial securing structure housed within the brush section that engages the protruding drive shaft of the handle section.

U.S. Pat. No. 5,974,615 discloses, referring FIG. 1 therein, an electric toothbrush (1) which incorporates a handle (2) and a brush attachment (3). The handle (2) houses an electric motor (8). Protruding from the handle (2) is a shaft (20), which is coupled to the electric motor (8). The brush attachment (3) can be mounted on the handle (2). The brush attachment (3) supports a bristle head (26) which can be coupled to the shaft (20), and from which protrude a multiplicity of bristles (4). In the operating mode, the bristle head (26) describes a rotary motion (49) and a stroke motion (50), with the frequency of the stroke movement (50) being higher, and preferably substantially higher, than the frequency of the rotary movement (49). The stroke movement (50) provides a poking action of the bristles (4), which serves to loosen plaque from dental surfaces. The rotary movement (49) serves to wipe away plaque loosened from the dental surfaces.

However, replaceable dental brush unit useful in an electric toothbrush that uses gear links for connecting and driving motions of bristle head by motors can be useful and/or desirable. For example, shift often has to be made of hard, expansive materials, e.g., metals. With proper design, e.g., groove thickness, gear links and components comprising such gear links can be made of relatively inexpensive materials, e.g., plastics, while still satisfying connecting and driving functions for dental brush unit useful in an electric toothbrush.

Accordingly, there is a need in the art for dental brush unit useful in an electric toothbrush using at least some gear links for connecting and driving motions of bristle head by motors. The present invention addresses this and other related needs in the art.

BRIEF SUMMARY OF THE INVENTION

Unless defined otherwise, all technical and scientific terms used herein have the same meaning as is commonly understood by one of ordinary skill in the art to which this invention belongs. All patents, applications, published applications and other publications and sequences from GenBank and other databases referred to herein are incorporated by reference in their entirety. If a definition set forth in this section is contrary to or otherwise inconsistent with a definition set forth in applications, published applications and other publications and sequences from GenBank and other data bases that are herein incorporated by reference, the definition set forth in this section prevails over the definition that is incorporated herein by reference.

As used herein, "a" or "an" means "at least one" or "one or more."

In one aspect, the present invention provides for a replaceable dental brush unit useful in an electric toothbrush using at least some gear links for connecting and driving motions of bristle head by motors. The gear links and components comprising such gear links can be made of any suitable materials or composite materials. Preferably, the gear links and components comprising such gear links are not made of metals. More preferably, the gear links and components comprising such gear links are made of plastics such as nylon, e.g., Ashlene nylons 6 and 66, toughened nylons, reinforced nylons, specialty-nylons and economy nylons or an acetal resin (e.g., Ashley Polymers, Inc., Brooklyn, N.Y.). Other resins such as polycarbonates, polyphenylene ethers, PBT and PET polyester can also be used.

In one specific embodiment, the present invention provides for a replaceable dental brush unit useful in an electric toothbrush, which replaceable dental brush unit comprises: a) a main body suitable for housing, form top to bottom, a gear unit connected to a bristle unit, a three-way exchange head, a moving rod and a base unit, said main body having a top opening transverse to the longitudinal axis of said main body for receiving said bristle unit and a bottom opening along the longitudinal axis of said main body for receiving said base unit, the wall opposing said top opening having a first protruding for receiving said gear unit; b) said bristle unit having a recess therein for connecting said bristle unit to said gear unit via a second protruding of said gear unit, said bristle unit also having attached bristles suitable for dental cleaning; c) said gear unit having a base plate, gear grooves attached to said base plate, a recess in said base plate at the side opposite to said gear grooves for securing said gear unit into said first protruding of main body, and a second protruding on said base plate at the side having attached gear grooves, said second protruding surrounded by and projecting beyond said gear grooves for securing said gear unit into said bristle unit; d) said three-way exchange head having a top portion and a bottom portion, said top portion having gear grooves that movably connected to said grooves of said gear unit, wherein the thickness of grooves of said three-way exchange head is less than or equal to the thickness of grooves of said gear unit, and said bottom portion having a recess for receiving and securing a third protruding of said moving rod; e) said moving rod having said top third protruding that fits into said bottom recess of said three-way exchange head, a middle opening, and preferably having a lug, for receiving and securing said moving rod to a corresponding linking element of an electric toothbrush, and a bottom portion having a recess for receiving a shaft connected to a motor unit of said electric toothbrush; and f) said base unit to secure said three-way exchange head and moving rod within said main body by providing an upward pressure, said base unit having a hollow space along the longitudinal axis of said main body allowing said shaft to pass by and connect to said moving rod, wherein, in operation, the linkages among said three-way exchange head, moving rod, base unit and shaft ensure that these units move as a single unit, said motor unit actuates said single unit, via said shift, to have an oscillating movement in a substantially singular plane that is parallel to said longitudinal axis of said main body, and said planar oscillating movement actuating said gear unit, via said gear connections between said three-way exchange head and said gear unit, to have a rotary movement, and said rotary movement, in turn, actuating said bristle unit to have a rotary movement.

The main body can be in any suitable shape, e.g., cylinder, rod, cubic, etc. The main body can be tapered or non-tapered, and can be enlarged at top, and/or bottom opening (s). The top and bottom openings can be in any suitable shape, e.g., cycle, square, rectangle or any other regular or irregular shapes. The top and bottom openings can have same or different shapes and/or sizes. The first protruding of the main body that is used for receiving the gear unit can be in any suitable shape and/or size, e.g., cylinder, rod, etc., provided that it is compatible with the recess in the base plate of the gear unit. The first protruding of the main body can be made as an integral part of the main body or can be made as a separate unit that can be attached to the main body after the main body is made.

As used herein, "top opening transverse to the longitudinal axis of said main body" means that the direction of the top opening is substantially non-opposing or substantially nonlinear to the longitudinal axis of the main body. Ordinarily, the angle between the direction of the top opening and the longitudinal axis of the main body is from about 45 degrees to about 135 degrees. Preferably, the angle between the two directions is from about 80 degrees to about 100 degrees. More preferably, the angle between the two directions is from about 85 degrees to about 95 degrees. Most preferably, the angle between the two directions is about, or is, 90 degrees.

As used herein, "a bottom opening along the longitudinal axis of said main body" means that the direction of the bottom opening is substantially opposing or linear to the longitudinal axis of the main body. Ordinarily, the angle between the bottom opening and the longitudinal axis of the main body is about 0–45 degrees or 135–180 degrees. Preferably, the angle between the two directions is about 0–10 degrees or 170–180 degrees. More preferably, the angle between the two directions is 0–5 degrees or 175–180 degrees. Most preferably, the angle between the two directions is about, or is, 0 or 180 degrees.

As used herein, "wall opposing said top opening" means that the wall, which can be a flat surface or a curved surface, and the plane containing the top opening is substantially linear. Ordinarily, the angle between the wall and the plane containing the top opening is about 0–45 degrees or 135–180 degrees. Preferably, the angle between the two directions is about 0–10 degrees or 170–180 degrees. More preferably, the angle between the two directions is 0–5 degrees or 175–180 degrees. Most preferably, the angle between the two directions is about, or is, 0 or 180 degrees.

The main body can optionally have a barrier underneath its top surface to help secure the gear unit within the main body and keep the gear unit from falling out of the top opening. In this regard, the base plate of the gear unit can be split into two layers: a small layer distal to the grooves of the gear unit and a larger layer that is proximal to the grooves of the gear unit. The signature diameter of the larger layer should equal to or slightly smaller than the signature diameter of the top opening of the main body so that the gear unit can be fit into the top opening of the main body. The total of the height of the barrier along the longitudinal axis of the main body and the signature diameter of the smaller layer of the base plate of the gear unit should equal to or be slightly smaller than the signature diameter of the larger layer of the base plate of the gear unit. In this way, once the gear unit is placed within the top opening of the main body, the barrier exerts a downward pressure on the gear unit. This downward pressure, in combination with the upward pressure exerted by the base unit, through the moving rod and the three-way exchange head, secures the gear unit within top opening of the main body and prevent it from falling out of the top opening.

The main body can also comprise one or more opening(s) between the top and bottom openings, e.g., near or at the height where the grooves of the gear unit and the three-way exchange head intersect or connect, for releasing fluid from the main body.

The bristle unit can be in any suitable shape, e.g., cylinder, rod, cubic, etc. In a preferred embodiment, the bristle unit has a smaller plate and a larger plate, said smaller plate having a recess therein for connecting said bristle unit to said gear unit via a second protruding of said gear unit, said larger plate having attached bristles suitable for dental cleaning. The smaller and larger plates can be in any suitable shape, e.g., cycle, square, rectangle or any other regular or irregular shapes. The recess in the smaller plate that is used for receiving the gear unit can be in any suitable shape and/or size, e.g., cylinder, rod, etc., provided that it is compatible with the second protruding of the gear unit. Any bristles suitable for dental cleaning can be used. The bristles can occupy entire or partial surface of the larger plate and can be distributed evenly or unevenly on the surface. The width of the top opening of the main body, the gear unit and the smaller plate of the bristle unit, all in a direction transverse to the longitudinal axis of the main body, can be such that after the bristle unit is connected to the gear unit and the gear unit is secured in the top opening of the main body, there is a small distance or space between the edge of the top opening and the larger plate. For example, this distance can range from about 0.05 mm to about 0.15 mm. The existence of this distance makes the bristle unit rotate smoothly. On the other hand, this distance cannot be too long, e.g., longer than 0.15 mm; for once this distance becomes too long, the bristle unit tends to wiggle when it rotates.

The gear unit can be in any suitable shape, e.g., cylinder, rod, cubic, etc. Its base plate can be in any suitable shape, e.g., cycle, square, rectangle or any other regular or irregular shapes. The recess in the base plate that is used for receiving the first protruding of the main body can be in any suitable shape and/or size, e.g., cylinder, rod, etc., provided that it is compatible with the first protruding of the main body. The second protruding of the gear unit that is used for receiving the bristle unit can be in any suitable shape and/or size, e.g., cylinder, rod, etc., provided that it is compatible with the recess in the smaller plate of the bristle unit. The thickness of the grooves of the gear unit must equal to or be slightly larger than the thickness of the grooves of the three-way exchange head. Preferably, The thickness of the grooves of the gear unit is slightly larger than the thickness of the grooves of the three-way exchange head because such a design improves resilience of the groove-groove connection between the gear unit and the three-way exchange head and the bristle will not stop rotate when it encounters pressure from teeth or other oral or dental tissues during brushing.

The three-way exchange head can be in any suitable shape, e.g., cylinder, rod, cubic, etc. Its top an bottom portions can be in any suitable shape, e.g., cycle, square, rectangle or any other regular or irregular shapes. The recess in the bottom portion that is used for receiving the top third protruding of the moving rod can be in any suitable shape and/or size, e.g., cylinder, rod, etc., provided that it is compatible with the top third protruding of the moving rod.

The moving rod can be in any suitable shape, e.g., cylinder, rod, cubic, etc. Its bottom portion can be in any suitable shape, e.g., cycle, square, rectangle or any other regular or irregular shapes. The middle opening and, preferably the lug, that is used for receiving and securing said moving rod to a corresponding linking element of an electric toothbrush can be in any suitable shape and/or size, e.g., cylinder, rod, etc., provided that it is compatible with the corresponding linking element of the electric toothbrush. The recess in the bottom portion that is used for receiving the shaft can be in any suitable shape and/or size, e.g., cylinder, rod, etc., provided that it is compatible with the shaft that is connected, directly or indirectly, to a motor unit.

One unique feature of the present dental brush unit is that, two units, i.e., the three-way exchange head and the moving rod, are used for making the connection between the motor unit and the gear unit. This design is advantageous because it has the flexibility of adjusting the total length of the three-way exchange head and the moving rod, along the longitudinal axis of the main body, after the three-way exchange head, the moving rod and the main body are separately made and ensures that the three-way exchange head and the moving rod be fit perfectly within the main body.

The base unit can be in any suitable shape, e.g., cylinder, rod, cubic, etc. its hollow space can be in any suitable shape and/or size, e.g., cylinder, rod, etc., provided that it is compatible with the shaft, i.e., can let the shaft pass by and does not interfere with shaft's movement.

In operation, the linkages among the three-way exchange head, moving rod, based unit and shaft ensure that these units move as a single unit, said motor, unit actuates said single unit, via said shaft, to have an oscillating movement in a substantially singular plane that is parallel to said longitudinal axis of said main body, and said planar oscillating movement actuating said gear unit, via said gear connections between said three-way exchange head and said gear unit, to have a rotary movement, and said rotary movement, in turn, actuating said bristle unit to have a rotary movement. Preferably, the single unit of the three-way exchange head, moving rod, based unit and shaft moves in a singular plane that coincides with the longitudinal axis of the main body.

The present replaceable dental brush unit can be used with any compatible electric toothbrush including any electric toothbrush disclosed in the U.S. Pat. Nos. 6,021,538, 5,974,615, 5,974,613, 5,943,723, 5,867,856, 5,862,558, 5,850,655, 5,842,244, 5,732,433, D388,958, 5,652,990, 5,577,285, 5,504,958, D353,490, 5,309,591, 5,289,604 and D266,117. Preferably, the present replaceable dental brush unit is used with Braun Oral-B electric toothbrush, e.g., Braun Oral-B 3D Plaque Remover and Braun Oral-B 3D Excel (Braun Aktiengesellschaft, Frankfurt, Germany).

In another specific embodiment, the present invention provides for a replaceable dental brush unit useful in an electric toothbrush, which replaceable dental brush unit consists essentially of, or consists of: a) a main body suitable for housing, form top to bottom, a gear unit connected to a bristle unit, a three-way exchange head, a moving rod and a base unit, said main body having a top opening transverse to the longitudinal axis of said main body for receiving said bristle unit and a bottom opening along the longitudinal axis of said main body for receiving said base unit, the wall opposing said top opening having a first protruding for receiving said gear unit; b) said bristle unit having a smaller plate and a larger plate, said smaller plate having a recess therein for connecting said bristle unit to said gear unit via a second protruding of said gear unit, said larger plate having attached bristles suitable for dental cleaning; c) said gear unit having a base plate, gear grooves attached to said base plate, a recess in said base plate at the side opposite to said gear grooves for securing said gear unit into said first protruding of main body, and a second protruding on said base plate at the side having attached gear grooves, said second protruding surrounded by and projecting beyond said gear grooves for securing said gear unit into said bristle unit; d) said three-way exchange head having a top portion and a bottom portion, said top portion having gear grooves that movably connected to said grooves of said gear unit, wherein the thickness of grooves of said three-way exchange head is less than or equal to the thickness of grooves of said gear unit, and said bottom portion having a recess for receiving and securing a third protruding of said moving rod; e) said moving rod having said top third protruding that fits into said bottom recess of said three-way exchange head, a middle opening, and preferably having a lug, for receiving and securing said moving rod to a corresponding linking element of an electric toothbrush, and a bottom portion having a recess for receiving a shaft connected to a motor unit of said electric toothbrush; and f) said base unit to secure said three-way exchange head and moving rod within said main body by providing an upward pressure, said base unit having a hollow space along the longitudinal axis of said main body allowing said shaft to pass by and connect to said moving rod, wherein, in operation, the linkages among said three-way exchange head, moving rod, base unit and shaft ensure that these units move as a single unit, said motor unit actuates said single unit, via said shift, to have an oscillating movement in a substantially singular plane that is parallel to said longitudinal axis of said main body, and said planar oscillating movement actuating said gear unit, via said gear connections between said three-way exchange head and said gear unit, to have a rotary movement, and said rotary movement, in turn, actuating said bristle unit to have a rotary movement.

BRIEF DESCRIPTION OF THE SEVERAL VIEWS OF THE DRAWINGS

FIG. 1A is a front view of the main body. FIG. 1B a side view of the main body. The main body is suitable for housing a gear unit, having a top opening 24, a bottom opening 26, and a first protrusion 28 for receiving a gear unit.

Figure 1A:
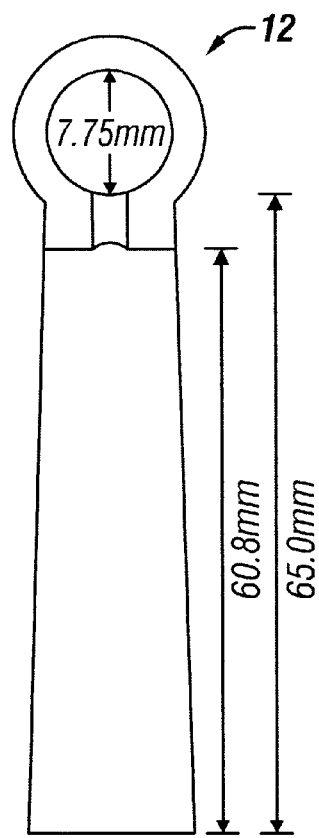
FIG. 1A–1B is a schematic view of an exemplary main body 12.
Figure 1B:
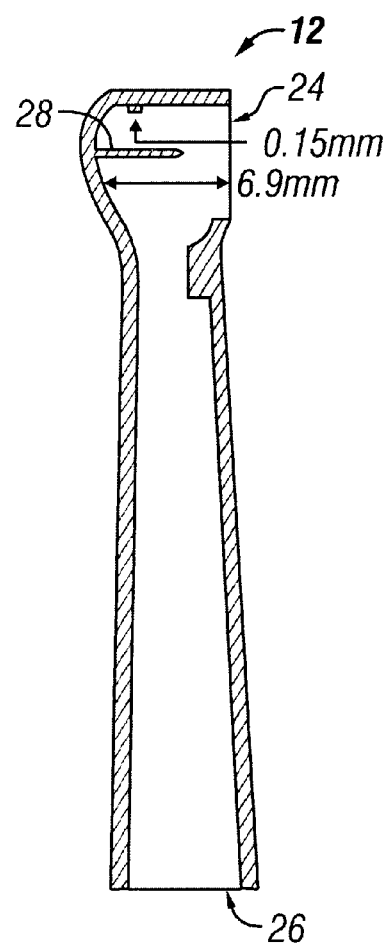
Figure 2:
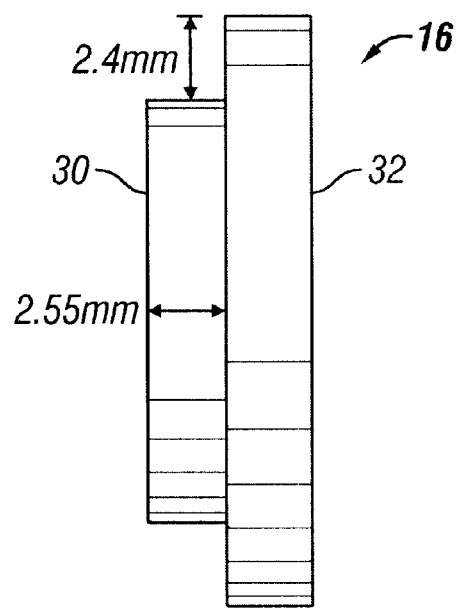
FIG. 2 is a schematic view of an exemplary bristle unit, (side view) 16, said bristle unit having a smaller plate 30 and a larger plate 32.
Figure 3:
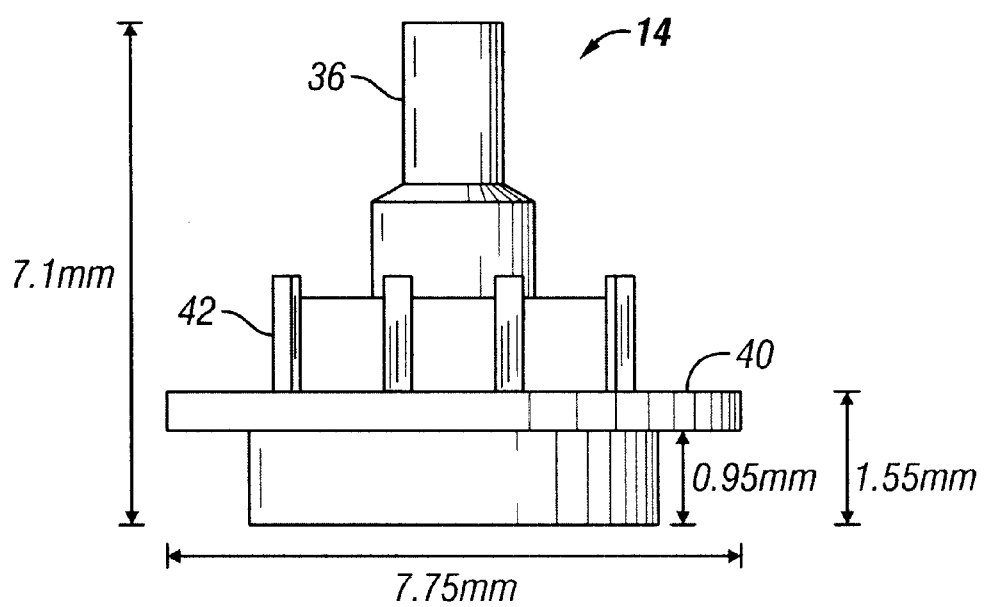
FIG. 3 is a schematic view of an exemplary gear unit (side view) 14. Said gear unit has a base plate 40, gear grooves 42 and a second protruding 36, by which the bristle unit is connected to the gear unit.
Figure 4:
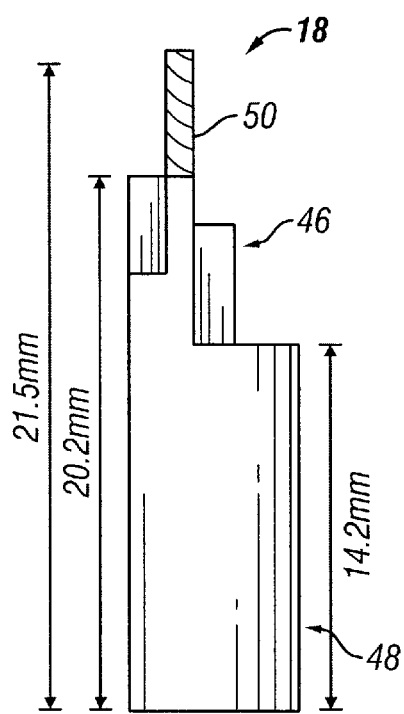
FIG. 4 is a schematic view of an exemplary three-way exchange head (side view) 18, having a top portion 46 and a bottom portion 48, and said top portion having gear grooves 50.
Figure 5:
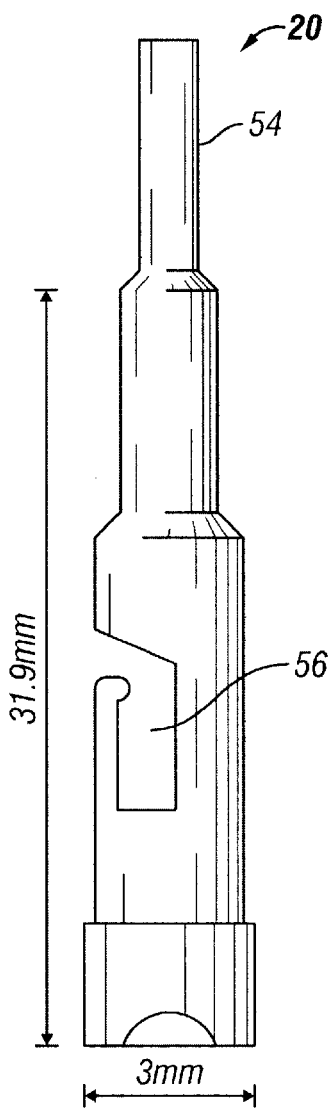
FIG. 5 is a schematic view of an exemplary moving rod (side view) 20, having a third protrusion 54 and a middle opening 56 for receiving and securing said moving rod to a corresponding linking element of an electric toothbrush.
Figure 6:
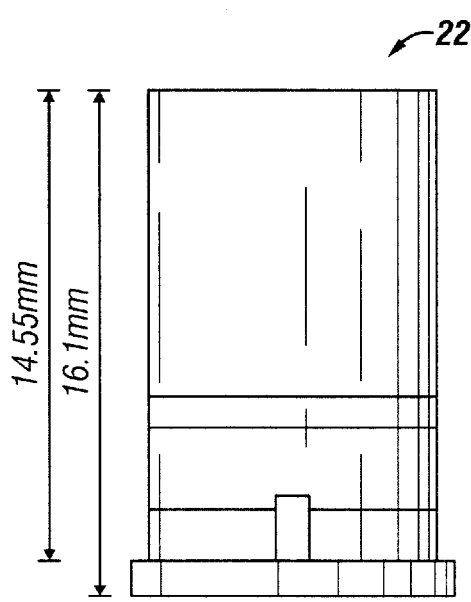
FIG. 6 is a schematic view of an exemplary base unit (side view) 22.
Figure 7:
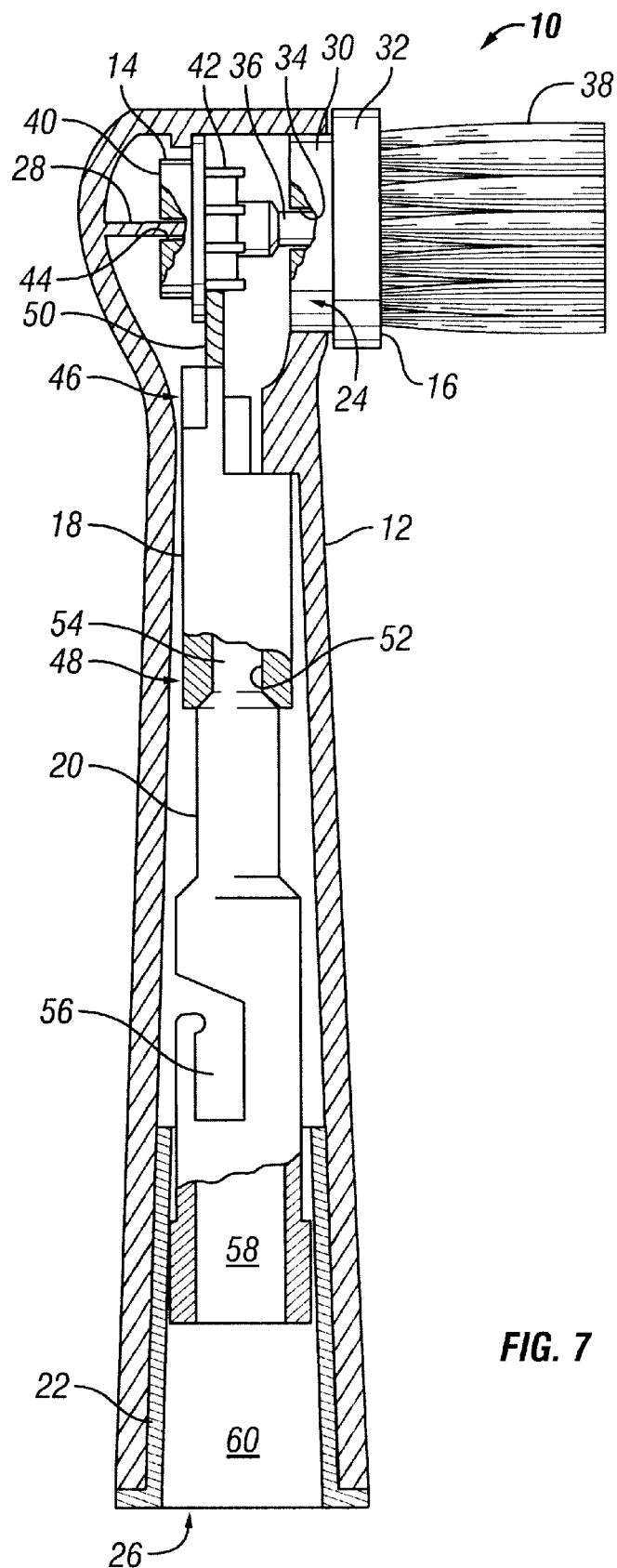
FIG. 7 illustrates the assembly of an exemplary main body, bristle unit with bristles 38 and a recess in the bristle unit 34, gear unit with the recess 44, three-way exchange head with a recess 52, moving rod with a recess 58 and base unit with a hollow space 60, to form an exemplary replaceable dental brush unit 10, wherein the bristle unit is connected to the gear unit and the connected gear and bristle units are connected to the top opening of the main body, and from bottom to top within the main body, the base unit is connected to the moving rod, which is connected to the three-way exchange head, which is in turn connected to the gear unit.

The above examples are included for illustrative purposes only and are not intended to limit the scope of the invention. Many variations to those described above are possible. Since modifications will be apparent to those of skill in this art, it is intended that this invention be limited only by the scope of the appended claims.

DETAILED DESCRIPTION OF THE INVENTION

Not Applicable

What is claimed is:

1. A replaceable dental, brush unit useful in an electric toothbrush, which replaceable dental brush unit comprises:

a) a main body suitable for housing, from top to bottom, a gear unit connected to a bristle unit, a three-way exchange head, a moving rod and a base unit, said main body having a top opening transverse to the longitudinal axis of said main body for receiving said bristle unit and a bottom opening along the longitudinal axis of said main body for receiving said base unit, the wall opposing said top opening having a first protruding for receiving said gear unit;

b) said bristle unit having a smaller plate and a larger plate, said smaller plate having a recess therein for connecting said bristle unit to said gear unit via a second protruding of said gear unit, said larger plate having attached bristles suitable for dental cleaning;

c) said gear unit having a base plate, gear grooves attached to said base plate, a recess in said base plate at the side opposite to said gear grooves for securing said gear unit into said first protruding of main body, and a second protruding on said base plate at the side having attached gear grooves, said second protruding surrounded by and projecting beyond said gear grooves for securing said gear unit into said bristle unit;

d) said three-way exchange head having a top portion and a bottom portion, said top portion having gear grooves that movably connected to said grooves of said gear unit, wherein the thickness of grooves of said three-way exchange head is less than or equal to the thickness of grooves of said gear unit, and said bottom portion having a recess for receiving and securing a third protruding of said moving rod;

e) said moving rod having said top third protruding that fits into said bottom recess of said three-way exchange head, a middle opening for receiving and securing said moving rod to a corresponding linking element of an electric toothbrush, and a bottom portion having a recess for receiving a shaft connected to a motor unit of said electric toothbrush; and f) said base unit to secure said three-way exchange head and moving rod within said main body by providing an upward pressure, said base unit having a hollow space along the longitudinal axis of said main body allowing said shaft to pass by and connect to said moving rod, wherein, in operation, the linkages among said three-way exchange head, moving rod, base unit and shaft ensure that these units move as a single unit, said motor unit actuates said single unit, via said shift, to have an oscillating movement in a substantially singular plane that is parallel to said longitudinal axis of said main body, and said planar oscillating movement actuating said gear unit, via said gear connections between said three-way exchange head and said gear unit, to have a rotary movement, and said rotary movement, in turn, actuating said bristle unit to have a rotary movement.

2. The replaceable dental brush unit of claim 1, wherein the top and/or the bottom openings are in a circular shape.

3. The replaceable dental brush unit of claim 1, wherein the first protruding of the main body is made as an integral part of the main body.

4. The replaceable dental brush unit of claim 1, wherein the angle between the direction of the top opening and the longitudinal axis of the main body is about 90 degrees.

5. The replaceable dental brush unit of claim 1, wherein the angle between the bottom opening and the longitudinal axis of the main body is about 0 or 180 degrees.

6. The replaceable dental brush unit of claim 1, wherein the wall opposing the top opening is a curved surface.

7. The replaceable dental brush unit of claim 1, wherein the angle between the wall opposing the top opening and the plane containing the top opening is about 0 or 180 degrees.

8. The replaceable dental brush unit of claim 1, wherein the main body further comprises a barrier underneath its top surface to help secure the gear unit within the main body and keep the gear unit from falling out of the top opening.

9. The replaceable dental brush unit of claim 1, wherein the main body further comprises an opening between the top and bottom openings for releasing fluid from the main body.

10. The replaceable dental brush unit of claim 1, wherein the bristles occupy entire or partial surface of the larger plate of the bristle unit.

11. The replaceable dental brush unit of claim 1, wherein the bristles are distributed evenly or unevenly on the surface of the larger plate of the bristle unit.

12. The replaceable dental brush unit of claim 1, wherein the width of the top opening of the main body, the gear unit and the smaller plate of the bristle unit, all in a direction transverse to the longitudinal axis of the main body is such that after the bristle unit is connected to the gear unit and the gear unit is secured in the top opening of the main body, there is a small distance or space between the edge of the top opening and the larger plate.

13. The replaceable dental brush unit of claim 12, wherein the small distance ranges from about 0.05 mm to about 0.15 mm.

14. The replaceable dental brush unit of claim 1, wherein the thickness of the grooves of the gear unit is slightly larger than the thickness of the grooves of the three-way exchange head.

15. The replaceable dental brush unit of claim 1, wherein in operation, the linkages among the three-way exchange head, moving rod, base unit and shaft ensure that these units move as a single unit, said motor unit actuates said single unit, via said shift, to have an oscillating movement in a singular plane that is parallel to said longitudinal axis of said main body.

16. The replaceable dental brush unit of claim 15, wherein in operation, the single unit of the three-way exchange head, moving rod, base unit and shaft moves in a singular plane that coincides with the longitudinal axis of the main body.

17. The replaceable dental brush unit of claim 1, wherein the main body, the gear unit, the bristle unit, the three-way exchange head, the moving rod and the base unit are made of a plastic material.

18. The replaceable dental brush unit of claim 17, wherein the plastic material is nylon or an acetal resin.

19. A replaceable dental brush unit useful in an electric toothbrush, which replaceable dental brush unit consists essentially of:

a) a main body suitable for housing, form top to bottom, a gear unit connected to a bristle unit, a three-way exchange head, a moving rod and a base unit, said main body having a top opening transverse to the longitudinal axis of said main body for receiving said bristle unit and a bottom opening along the longitudinal axis of said main body for receiving said base unit, the wall opposing said top opening having a first protruding for receiving said gear unit;

b) said bristle unit having a smaller plate and a larger plate, said smaller plate having a recess therein for connecting said bristle unit to said gear unit via a second protruding of said gear unit, said larger plate having attached bristles suitable for dental cleaning;

c) said gear unit having a base plate, gear grooves attached to said base plate, a recess in said base plate at the side opposite to said gear grooves for securing said gear unit into said first protruding of main body, and a second protruding on said base plate at the side having attached gear grooves, said second protruding surrounded by and projecting beyond said gear grooves for securing said gear unit into said bristle unit;

d) said three-way exchange head having a top portion and a bottom portion, said top portion having gear grooves that movably connected to said grooves of said gear unit, wherein the thickness of grooves of said three-way exchange head is less than or equal to the thickness of grooves of said gear unit, and said bottom portion having a recess for receiving and securing a third protruding of said moving rod;

e) said moving rod having said top third protruding that fits into said bottom recess of said three-way exchange head, a middle opening for receiving and securing said moving rod to a corresponding linking element of an electric toothbrush, and a bottom portion having a recess for receiving a shaft connected to a motor unit of said electric toothbrush; and f) said base unit to secure said three-way exchange head and moving rod within said main body by providing an upward pressure, said base unit having a hollow space along the longitudinal axis of said main body allowing said shaft to pass by and connect to said moving rod, wherein, in operation, the linkages among said three-way exchange head, moving rod, base unit and shaft ensure that these units move as a single unit, said motor unit actuates said single unit, via said shift, to have an oscillating movement in a substantially singular plane that is parallel to said longitudinal axis of said main body, and said planar oscillating movement actuating said gear unit, via said gear connections between said three-way exchange head and said gear unit, to have a rotary movement, and said rotary movement, in turn, actuating said bristle unit to have a rotary movement.

20. A replaceable dental brush unit useful in an electric toothbrush, which replaceable dental brush unit consists of:

a) a main body suitable for housing, form top to bottom, a gear unit connected to a bristle unit, a three-way exchange head, a moving rod and a base unit, said main body having a top opening transverse to the longitudinal axis of said main body for receiving said bristle unit and a bottom opening along the longitudinal axis of said main body for receiving said base unit, the wall opposing said top opening having a first protruding for receiving said gear unit;

b) said bristle unit having a smaller plate and a larger plate, said smaller plate having a recess therein for connecting said bristle unit to said gear unit via a second protruding of said gear unit, said larger plate having attached bristles suitable for dental cleaning;

c) said gear unit having a base plate, gear grooves attached to said base plate, a recess in said base plate at the side opposite to said gear grooves for securing said gear unit into said first protruding of main body, and a second protruding on said base plate at the side having attached gear grooves, said second protruding surrounded by and projecting beyond said gear grooves for securing said gear unit into said bristle unit;

d) said three-way exchange head having a top portion and a bottom portion, said top portion having gear grooves that movably connected to said grooves of said gear unit, wherein the thickness of grooves of said three-way exchange head is less than or equal to the thickness of grooves of said gear unit, and said bottom portion having a recess for receiving and securing a third protruding of said moving rod;

e) said moving rod having said top third protruding that fits into said bottom recess of said three-way exchange head, a middle opening for receiving and securing said moving rod to a corresponding linking element of an electric toothbrush, and a bottom portion having a recess for receiving a shaft connected to a motor unit of said electric toothbrush; and f) said base unit to secure said three-way exchange head and moving rod within said main body by providing an upward pressure, said base unit having a hollow space along the longitudinal axis of said main body allowing said shaft to pass by and connect to said moving rod, wherein, in operation, the linkages among said three-way exchange head, moving rod, base unit and shaft ensure that these units move as a single unit, said motor unit actuates said single unit, via said shift, to have an oscillating movement in a substantially singular plane that is parallel to said longitudinal axis of said main body, and said planar oscillating movement actuating said gear unit, via said gear connections between said three-way exchange head and said gear unit, to have a rotary movement, and said rotary movement, in turn, actuating said bristle unit to have a rotary movement.

* * * * *